United States Patent
Kim et al.

(10) Patent No.: US 8,202,714 B2
(45) Date of Patent: Jun. 19, 2012

(54) PSEUDOMONAS SP. HN-72 AND PURIFICATION METHOD OF 2,6-NAPHTHALENE DICARBOXYLIC ACID USING THE SAME

(75) Inventors: Sung Kyoon Kim, Gyeonggi-Do (KR); Yong Bok Choi, Gyeonggi-Do (KR); Dong Sung Kim, Gyeonggi-Do (KR); Jong Hwan Lee, Gyeonggi-Do (KR); So Young Kim, Gwanak-Gu (KR)

(73) Assignee: Hyosung Corporation, Seoul (KR)

( * ) Notice: Subject to any disclaimer, the term of this patent is extended or adjusted under 35 U.S.C. 154(b) by 886 days.

(21) Appl. No.: 12/094,565

(22) PCT Filed: Jan. 16, 2006

(86) PCT No.: PCT/KR2006/000166
§ 371 (c)(1),
(2), (4) Date: Oct. 7, 2008

(87) PCT Pub. No.: WO2007/061155
PCT Pub. Date: May 31, 2007

(65) Prior Publication Data
US 2009/0215136 A1    Aug. 27, 2009

(30) Foreign Application Priority Data
Nov. 24, 2005   (KR) .................. 10-2005-0112946

(51) Int. Cl.
*C12P 7/44*   (2006.01)
(52) U.S. Cl. ..................................... 435/142; 435/253.3
(58) Field of Classification Search .................. None
See application file for complete search history.

(56) References Cited

U.S. PATENT DOCUMENTS
5,030,568 A    7/1991    Carlson et al.

FOREIGN PATENT DOCUMENTS
| KR | 10-2004-0061548 | 7/2004 |
| KR | 10-2005-0071188 | 7/2005 |
| KR | 10-2005-0007216 | 1/2006 |
| WO | WO 2007/069805 A1 | 6/2007 |

OTHER PUBLICATIONS

Worsey et al., J. Bact., 1975, vol. 124, pp. 7-13).*
Kim et al. "A novel biotransformation of 2-formyl-6 naphthoic acid to 2,6-naphthalene dicarboxylic acid by *Pseudomonas* sp. for the purification of crude 2,6-naphthalene dicarboxylic acid." *Biotecchnol Lett* (2008) 30:329-333. Abstract Only.
Kiyohara et al. "The Catabolism of Phenanthrene and Naphthalene by Bacteria." *Journal of General Microbiology* (1978), 105, 69-75.
Harayama et al. "Characterization of Five Genes in the Upper-Pathway Operon of TOL Plasmid pWW0 from *Pseudomonas putida* and Identification of the Gene Products." *Journal of Bacteriology*, Sep. 1989, p. 5048-5055.
Miayachi et al. "Microbial Oxidation of Dimethylnaphthalene Isomers." *Applied and Environmental Microbiology*. May 1993, p. 1504-1506.

* cited by examiner

*Primary Examiner* — Irene Marx
(74) *Attorney, Agent, or Firm* — Merchant & Gould P.C.

(57) ABSTRACT

Provided are a novel microorganism and a method for purifying 2,6-naphthalene dicarboxylic acid with high purity using the microorganism. The microorganism is *Pseudomonas* sp. Strain HN-72 isolated from soil and has the ability to convert 2-formyl-6-naphthoic acid contained as an impurity in a crude naphthalene dicarboxylic acid, which is an oxidation product of 2,6-dimethylnaphthalene, to 2,6-naphthalene dicarboxylic acid. The *Pseudomonas* sp. strain HN-72 has excellent effects in producing high-purity 2,6-naphthalene dicarboxylic acid in high yield.

11 Claims, 1 Drawing Sheet

```
TTGCGAGCGTGCTACAGCAGTCAGCGGATGACGCGAGCTCGCTCCCTGAT
TCAGCGGAGGACGGGTGAGTAATGCCTAGGATTCTGGCTGGTAGTGGGGG
ACAACGTCTCGATAGGAACGCTAATACCGCATACGTCCTACGTGAGATAG
CATTAGACCTTCGGACCTTGCGCTATCAGATGAGCCTTGGTCGGATTAGC
TAGATGGTGCAGTAATGGCTCAGGATGGCGACGATCCGTAACTGGTCTGA
GAGGATGATCACTCACACTGGAACTGAGACACGGTCCAGGCTCCTACGAG
AGCGGGCAGTGGTGAATATTGGACAATGGGCGACAGCCTGATCCAGGCAT
GCAGCGTGTGTGAAGAAGGTCTTCGGATTGTAAAGCACTTTAAGTTGTGA
GGAAGGCGAGTAAGTTAATACCTTGCTGTCATGACGTTACCGAAAGAATA
AGCACCGGCTAACTCTGAGCCAGCAGCTGCGGTAATACAGATGGTGCAAG
CGTTAATCGGAATTACTGGGCGTATAGCGCGCGTAGGTGGTTTGTTAAGT
TGGATGTGAAAGCCCCGGGCTCAACCTGGGAACTGAATCCACCACTGGCA
AGCTAGAGTACGGTAGAGGGTGCTGGAATATCCTGTGTAGCGGTGAAATG
CGTAGATATAGGAAGGAACACCAGTGGCTACAGCGACCACCTGGACTGAT
```

PSEUDOMONAS SP. HN-72 AND PURIFICATION METHOD OF 2,6-NAPHTHALENE DICARBOXYLIC ACID USING THE SAME

TECHNICAL FIELD

The present invention relates to a novel microorganism capable of converting 2-formyl-6-naphthoic acid (FNA) contained as an impurity in a crude naphthalene di-carboxylic acid (cNDA), which is an oxidation product of 2,6-dimethyl-naphthalene (2,6-DMN), to 2,6-naphthalene dicarboxylic acid (NDA), and a method for purifying 2,6-naphthalene dicarboxylic acid with high purity using the microorganism.

BACKGROUND ART

Diesters of naphthalene dicarboxylic acids are useful for the preparation of a variety of polymeric materials, such as polyester and polyamide. A particularly useful diester is dimethyl-2,6-naphthalene dicarboxylate (NDC). NDC can be condensed with ethylene glycol to form poly(ethylene 2,6-naphthalate) (PEN), which is a high-performance polyester material. Fibers and films made from PEN exhibit high strength and superior thermal properties, compared to those made from poly(ethylene terephthalate) (PET). Based on these advantages, PEN is highly suitable for use in the production of commercial articles, such as thin films, which can be used for the manufacture of magnetic recording tapes and electronic components. In addition, since PEN is highly resistant to the diffusion of gases, particularly carbon dioxide, oxygen and water vapor, films made from PEN are useful for the manufacture of food containers, especially hot-fill food containers. PEN can also be used to produce reinforced fibers useful for the manufacture of tire cords.

NDC is currently produced by oxidizing 2,6-DMN to prepare a crude naphthalene dicarboxylic acid (cNDA) and esterifying the cNDA. At present, NDC is used as a major raw material for the synthesis of PEN. However, some problems are presented when NDC is used as a raw material for the synthesis of PEN, compared to when 2,6-naphthalene dicarboxylic acid (NDA) is used. Firstly, water is formed as a by-product during the condensation of NDA, whereas methanol is formed as a by-product in the case of NDC, thus risking the danger of explosion. Secondly, since pure NDC is produced by esterifying NDA and purifying the esterification product, one additional processing step is involved, compared to the use of NDA. Thirdly, the use of NDC is not suitable in view of the use of existing PET production facilities. Despite the problems associated with the use of NDC, NDC is preferentially used to produce PEN because it is still difficult to produce purified NDA having a purity necessary for the synthesis of PEN.

2,6-Dimethylnaphthalene (2,6-DMN) is oxidized to form a cNDA containing various impurities, such as 2-formyl-6-naphthoic acid (FNA), 2-naphthoic acid and trimellitic acid. Particularly, the presence of FNA in a cNDA stops the polymerization for the production of PEN, thus adversely affecting the physical properties of the final polymer (i.e. PEN). It is thus essential to remove FNA present in a cNDA, but difficulties exist in removing FNA.

Under these circumstances, much research has been conducted on methods for the removal of FNA present in a cNDA or purification of NDA. For example, NDA is produced by i) recrystallizing a cNDA, ii) oxidizing a cNDA one more time, or ii) treating a cNDA with methanol to produce NDC and hydrating the NDC. Further, purified NDA is produced by hydrogenation of a cNDA. On the other hand, many processes, e.g., solvent treatment, melting/crystallization, high-pressure crystallization and supercritical extraction, have been employed to purify NDA, but they have not been successful in producing NDA with a satisfactory purity. The processes can be employed to increase the purity of NDA but cause low yield of NDA, which makes the processes difficult to practice industrially.

DISCLOSURE OF INVENTION

Technical Problem

The present invention has been made in view of the problems of the prior art, and it is an object of the present invention to provide a novel method for producing high-purity NDA by selectively converting FNA, which is an impurity contained in a cNDA, to NDA by biological treatment using a microorganism.

Technical Solution

In accordance with one aspect of the present invention, there is provided *Pseudomonas* sp. HN-72 (Accession No. KCTC 10819BP) that has the ability to convert 2-formyl-6-naphthoic acid to 2,6-naphthalene dicarboxylic acid.

In accordance with another aspect of the present invention, there is provided a method for purifying 2,6-naphthalene dicarboxylic acid with high purity using the *Pseudomonas* sp. HN-72 (Accession No. KCTC 10819BP).s.

Advantageous Effects

The *Pseudomonas* sp. strain HN-72 of the present invention has excellent effects in converting 2-formyl-6-naphthoic acid to 2,6-naphthalene dicarboxylic acid. Therefore, the *Pseudomonas* sp. HN-72 of the present invention contributes to the production of high-purity 2,6-naphthalene dicarboxylic acid in an economical and environmentally friendly manner and is thus very important for use in industrial applications.

BRIEF DESCRIPTION OF THE DRAWINGS

The above and other objects, features and other advantages of the present invention will be more clearly understood from the following detailed description taken in conjunction with the accompanying drawing, in which:

FIG. 1 shows a partial sequence of 16S rDNA of *Pseudomonas* sp. strain HN-72 of the present invention.

BEST MODE FOR CARRYING OUT THE INVENTION

A more detailed description of a novel strain according to the present invention will be provided below.

The present inventors have succeeded in isolating a novel strain having the ability to convert FNA to NDA from soil. The novel strain of the present invention was identified as a bacterium belonging to the genus *Pseudomonas* by 16s rDNA partial sequencing, and termed *Pseudomonas* sp. HN-72. The *Pseudomonas* sp. strain HN-72 was deposited at GenBank of the Korea Research Institute of Bioscience and Biotechnology (KRIBB), 111 Gwahangno, Yuseong-gu, Daejeon 305-806, Korea, which is an international depository authority, under the accession number of KCTC-10819BP on Jun. 21, 2005. The *Pseudomonas* sp. strain HN-72 of the present invention is a microorganism that oxidizes 2-naphthaldehyde having a formyl group at the same position as that of 2-formyl-6-naphthoic acid to convert the formyl group of the 2-naphthaldehyde to a carboxyl group. Accordingly, the strain of the present invention is highly capable of selectively converting 2-formyl-6-naphthoic acid contained in a crude naphthalene dicarboxylic acid, which is an oxidation product of 2,6-dimethylnaphthalene, to 2,6-naphthalene dicarboxylic acid. The *Pseudomonas* sp. strain FIN-72 of the present invention has considerably improved conversion ability when compared to the *Bacillus* sp. strain F-3, which is described in the already filed patent application (Korean Patent Application No. 10-2002-0087819).

The *Pseudomonas* sp. strain HN-72 (Accession No. KCTC-10819BP) of the present invention can be easily cultured in a liquid medium in a wide temperature range of 25 to 37° C.

A method for purifying 2,6-naphthalene dicarboxylic acid using the *Pseudomonas* sp. strain HN-72 of the present invention will be described in more detail below.

Specifically, the method of the present invention comprises the steps of 1) inoculating the *Pseudomonas* sp. HN-72 (Accession No. KCTC 10819BP) onto a liquid medium, culturing the inoculum with shaking, collecting the cultured bacteria, and washing the collected bacteria with physiological saline to activate the bacteria, 2) mixing a crude naphthalene dicarboxylic acid as a matrix with a buffer solution and adjusting the pH of the mixed solution to prepare a reaction solution for subsequent purification, and 3) reacting the active bacteria (*Pseudomonas* sp. HN-72) prepared in step 1) with the reaction solution prepared in step 2) to convert 2-formyl-6-naphthoic acid contained in the crude naphthalene dicarboxylic acid to 2,6-naphthalene dicarboxylic acid, so that the purity of the 2,6-naphthalene dicarboxylic acid is increased.

As the liquid medium used to culture the *Pseudomonas* sp. strain HN-72 in step 1), a Luria-Bertani (LB) or M9 minimal medium may be used without limitation. The step of culturing the *Pseudomonas* sp. strain HN-72 with shaking is preferably performed at a temperature ranging from 25 to 37° C. and more preferably at a temperature of 30° C.

The bacteria (*Pseudomonas* sp. HN-72) collected after shaking is preferably stored in a freezer at 4° C. or lyophilized such that the activity of the bacteria is maintained as long as possible.

The kind of the buffer solution used in step 2) is not especially restricted. As the buffer solution, there may be used water, potassium phosphate (KH2PO4)-KOH buffer, sodium pyrophosphate-HCl buffer, boric acid-NaOH buffer, sodium borate-HCl buffer, or the like. Potassium phosphate-KOH or boric acid-NaOH buffer is preferably used.

The reaction with the cNDA decreases the pH of the reaction solution. Specifically, the pH of the reaction solution is within the range of 7.0-8.0 after completion of the reaction with the cNDA in the reaction solution. Accordingly, a potassium phosphate (KH2PO4)-KOH buffer at a pH of 6.0-8.0 is preferably used as the buffer solution. At this time, it is preferred that the buffer solution have a concentration of 0.01 to 100 mM.

On the other hand, the pH of the reaction solution in the subsequent purification reaction (step 3)) of the cNDA is a very important reaction factor. In step 2), the pH of the mixed solution is preferably adjusted to the range of 7.5 to 8.3. When the reaction solution has an initial pH lower than 7.5 or higher than 8.3, no reaction proceeds in step 3).

In step 2), an organic solvent may be additionally added to the mixed solution for the purpose of dissolving the cNDA. Examples of preferred organic solvents include dimethylsulfoxide (DMSO), N,N-dimethylformamide (DMF), N,N-dimethylacetamide (DMA), and tetrahydrofuran (THF). Of these, dimethylsulfoxide is most preferred in terms of enzymatic activity. The organic solvent is preferably added at a concentration of 0.01 to 10%. More preferably, no organic solvent is added. The addition of the organic solvent at a concentration exceeding 10% causes lysis of the cell membranes of the microorganism, resulting in inhibition of the reaction.

In step 3), the reaction is preferably conducted in a temperature range of 30 to 50° C. When the reaction temperature is outside this range, a marked decrease in the activity of the bacteria is undesirably caused.

MODE FOR THE INVENTION

Hereinafter, the constitution and effects of the present invention will be specifically explained with reference to the following examples. However, these examples are given for the purpose of illustration and are not to be construed as limiting the scope of the invention.

EXAMPLES

Example 1

Isolation of Strain

Soil was sampled from wastewater treatment plants, oil reservoirs and gas stations located in Gyeonggi Do, Korea. 5 g of each of the soil samples was added to 50 ml of a 0.85% physiological saline solution, shaken and filtered to obtain a filtrate. The filtrate was diluted to an appropriate level, plated on an LB solid medium containing a cNDA, and cultured in an incubator at 30° C. As a result of the culture, 200 microorganisms were isolated.

Only microorganisms that decompose 2-naphthaldehyde having a formyl group at the same position as that of FNA were primarily screened in accordance with the following procedure. First, each of the 200 microorganisms was inoculated onto 1 ml of an LB liquid medium and cultured with shaking at 200 rpm and 30° C. for 16 hours.

The cultures were centrifuged to collect the corresponding bacteria. The collected bacteria were suspended in 1 ml of a 0.85% physiological saline solution. Separately, 0.2 ml of a 2-naphthaldehyde solution (50 μg/ml in DMSO) was added to sample cuvettes containing 3 ml of a β-NAD solution (0.25 mg/ml in 100 mM KH2PO4-KOH (pH 8.0)), and 0.2 ml of DMSO was added to a blank cuvette containing 3 ml of a β-NAD solution (0.25 mg/ml in 100 mM KH2PO4-KOH (pH 8.0)). The cuvettes were placed in respective spectrometer and stabilized for 3 minutes. 5 minutes after the addition of 0.05 ml of the microorganism suspensions to the respective sample cuvettes, the absorbance of the mixtures was measured at 340 nm. The absorbance values of the mixtures in the sample cuvettes were compared with the absorbance value of the blank cuvette to confirm the oxidation of the formyl group of the 2-naphthaldehyde to a carboxyl group. As a result, four microorganisms having an absorbance difference of a minimum of 0.1 were isolated. Each of the four primarily screened microorganisms was inoculated onto an LB liquid medium and cultured with shaking at 200 rpm and 30° C. for 16 hours. The cultures were centrifuged to collect the corresponding bacteria, washed with a 0.85% physiological saline solution, and reacted with solutions having the composition indicated in Table 1 in a reaction bath at 30° C. for 3 hours. The reaction products were analyzed by high-performance liquid chromatography (HPLC) to finally screen a strain that was highly capable of removing FNA. The HPLC analysis was performed under the conditions indicated in Table 2. The HPLC analysis shows that the strain termed HN-72 was highly capable of decomposing FNA.

TABLE 1

Reaction solution for final screening

| Composition | Volume (ml) | Remarks |
|---|---|---|
| 50 mM $KH_2PO_4$—KOH (pH 8.0) | 37.5 | |
| cNDA solution | 4 | * Concentration of cNDA solution: 50 mg/ml |
| DMSO | 2.5 | * Final concentration in reaction solution: 5% |
| Microorganism suspension | 5 | * Concentration of microorganism suspension: 0.5 g (w.w)/ml |
| Total | 50 | |

TABLE 2

Conditions for HPLC analysis

| HPLC | LC 10-ADVP (Shimadzu) | | |
|---|---|---|---|
| Column | Xterra ™ RP18 (4.6 × 250 mm, Waters) | | |
| Detector | UV 240 nm | | |
| Column temp. | 40° C. | | |
| Flow rate | 1 ml/min. | | |
| Injection volume | 20 μl | | |
| | Time (min.) | 0.3% phosphoric acid | Acetonitrile |
| Mobile phase | 0 | 98 | 2 |
| | 5 | 92 | 8 |
| | 28 | 52 | 48 |
| | 30 | 20 | 80 |
| | 35 | 5 | 95 |
| | 36 | 98 | 2 |
| | 49 | 98 | 2 |

Example 2

(1) Identification of Microorganism 16S rDNA partial sequencing of the strain isolated in Example 1 was performed to identify the strain. The results are shown in FIG. 1. According to the results, the strain was identified as a bacterium belonging to the genus *Pseudomonas*. The strain was termed *Pseudomonas* sp. HN-72 and deposited at GenBank of the Korea Research Institute of Bioscience and Biotechnology (KRIBB), which is an international depository authority, under the accession number of KCTC-10819BP on Jun. 21, 2005.

The morphology and biochemical characteristics of the strain (*Pseudomonas* sp. HN-72) were determined, and the results are summarized in Tables 3 and 4.

TABLE 3

Characteristics of *Pseudomonas* sp. HN-72

| Test | Characterization |
|---|---|
| Gram stain | Negative |
| Cell morphology | Rod |
| Optimal growth temperature | 25-30° C. |
| Oxidase | Positive |
| Denitrification | Negative |
| Gelatin degradation | Negative |

TABLE 3-continued

Characteristics of *Pseudomonas* sp. HN-72

| Test | Characterization |
|---|---|
| Starch degradation | Negative |
| Catechol degradation | Negative |

TABLE 4

Utilization of carbon sources by *Pseudomonas* sp. HN-72

| Carbohydrate | Utilization ability | Carbohydrate | Utilization ability |
|---|---|---|---|
| Glucose | + | Lactose | + |
| Fructose | + | Citrate | + |
| Galactose | − | Glycerol | + |
| Arabinose | − | Phthalate | − |
| Rhamnose | + | Isopropanol | − |
| Trehalose | − | Butanol | + |
| Maltose | − | Sorbitol | − |
| Lactose | − | Mannitol | − |
| Sucrose | − | Ribose | + |
| Starch | − | Succinate | + |

(2) Comparison of *Pseudomonas* Sp. HN-72 with Known Strain

The reaction efficiency of the *Pseudomonas* sp. strain HN-72 was compared with that of the *Bacillus* sp. strain F-3 having the same ability to remove FNA, which is described in the already filed patent application (Korean Patent Application No. 10-2002-0087819). After the strains *Bacillus* sp. F-3 and *Pseudomonas* sp. HN-72 were added to the reaction solutions having the composition indicated in Table 1, the respective experimental groups were reacted under the same conditions. The HPLC analysis was performed under the conditions indicated in Table 2.

The two strains were added to reaction solutions containing a cNDA at concentrations of 1% and 5%, respectively, and reacted at 30° C. The reaction solutions were analyzed, and the results are shown in Table 5.

From the results of Table 5, it could be confirmed that the *Pseudomonas* sp. HN-72 could also react with the cNDA at a higher concentration and was highly capable of converting FNA to NDA, i.e. showed high NDA yield and purity, when compared to the *Bacillus* sp. strain F-3.

TABLE 5

Changes in contents of NDA and FNA in cNDA reaction solutions by *Pseudomonas* sp. HN-72 and *Bacillus* sp. F-3

| Strain | cNDA concentration | Reaction time | Contents (%) in reaction solutions | |
|---|---|---|---|---|
| | | | NDA | FNA |
| *Pseudomonas* sp. HN-72 | 1% | 0 | 89.76 | 6.43 |
| | | 30 min. | 94.28 | 4.78 |
| | | 1 hr. | 95.04 | 0.80 |
| | 5% | 0 | 88.96 | 6.46 |
| | | 30 min. | 91.79 | 3.56 |
| | | 1 hr. | 94.14 | 2.03 |
| *Bacillus* sp. F-3 | 1% | 0 | 90.24 | 6.01 |
| | | 30 min. | 89.68 | 4.09 |
| | | 1 hr. | 89.44 | 2.70 |
| | 5% | 0 | 89.22 | 6.01 |

TABLE 5-continued

Changes in contents of NDA and FNA in cNDA reaction solutions by *Pseudomonas* sp. HN-72 and *Bacillus* sp. F-3

| Strain | cNDA concentration | Reaction time | Contents (%) in reaction solutions | |
|---|---|---|---|---|
| | | | NDA | FNA |
| | | 30 min. | 89.39 | 6.46 |
| | | 1 hr. | 89.82 | 6.39 |

Example 3

Influence of Reaction Temperature cNDA reaction solutions having the composition indicated in Table 6 were reacted at 30, 35, 40 and 50° C. to confirm the optimal reaction temperature of the cNDA reaction solutions. At this time, an enzyme solution was prepared by inoculating the *Pseudomonas* sp. HN-72 onto an LB liquid medium, culturing the inoculum in a shaking incubator at 30° C. for 16 hours, and centrifuging the culture to collect the cultured bacteria, washing the collected bacteria with a 0.85% physiological saline solution, and suspending the washed bacteria in a 0.85% physiological saline solution. The final concentration of the bacteria in the reaction solutions was adjusted to 0.05 μl ml. As apparent from the results of Table 7, a higher reaction temperature was advantageous for the reaction and a temperature of 40° C. or higher did not cause any substantial change in the reaction.

TABLE 6

| Composition | Content | Remarks |
|---|---|---|
| 50 mM $KH_2PO_4$—KOH (pH 8.0) | 42.5 ml | |
| cNDA | 2.5 g | * Final concentration in reaction solution: 5% |
| DMSO | 2.5 ml | * Final concentration in reaction solution: 5% |
| Microorganism suspension | 5 ml | *Concentration of microorganism suspension: 0.5 g (w.w)/ml |
| Total | 50 ml | |

TABLE 7

Changes in NDA content/FNA content in cNDA reaction solutions at different reaction temperatures

| | 30° C. | 35° C. | 40° C. | 50° C. |
|---|---|---|---|---|
| 0 | 90.82%/5.66% | 90.35%/6.08% | 89.51%/6.05% | 89.73%/5.95% |
| 30 min. | 93.16%/3.16% | 94.72%/1.55% | 95.09%/0.44% | 95.01%/0.45% |
| 1 hr. | 94.63%/1.06% | 95.39%/0.19% | 95.55%/0.06% | 95.49%/0.05% |

Example 4

Influence of Dimethylsulfoxide (DMSO)

Since the cNDA as a matrix was insoluble in an aqueous solution, dimethyl-sulfoxide (DMSO) was used as a solvent to carry out the reaction. To evaluate the influence of DMSO on the reaction, changes in the content ratio (NDA content/FNA content) in the cNDA reaction solutions having the composition indicated in Table 6 were compared by varying the concentration of DMSO as indicated in Table 8. That is, 5% cNDA reaction solutions containing a 50 mM potassium phosphate (KH2PO4)-KOH buffer (pH 8.0) and DMSO at concentrations of 0%, 5% and 10% were reacted at 40° C. The results are shown in Table 8. As can be seen from the data shown in Table 8, the cNDA reaction solution containing no DMSO showed the best results.

TABLE 8

Changes in NDA content/FNA content in cNDA reaction solutions with varying concentrations of DMSO

| | 0% | 5% | 10% |
|---|---|---|---|
| 0 | 91.09%/2.54% | 90.39%/2.86% | 90.51%/2.75% |
| 30 min. | 92.68%/0.31% | 92.16%/1.19% | 91.09%/2.44% |
| 1 hr. | 93.23%/0% | 92.76%/0.46% | 91.55%/1.36% |

Example 5

Influence of Buffer Solutions

In this experiment, various buffer solutions, each of which has a similar pH range, were used to evaluate effects according to the kind of the buffer solutions. At this time, the buffer solutions were used to maintain the homeostasis of the microorganism bacteria. This experiment was conducted by varying the buffer solution in the reaction solutions having the composition indicated in Table 6.

Potassium phosphate (KH2PO4)-KOH buffer, sodium pyrophosphate-HCl buffer, boric acid-NaOH buffer and sodium borate-HCl buffer were used in the experiment. The concentration and pH of the buffer solutions were adjusted to 50 mM and 8.0, respectively.

The experimental results are shown in Table 9. The results indicate that better results were obtained when the potassium phosphate (KH2PO4-KOH) buffer and boric acid-NaOH were used. The reaction with the cNDA decreases the pH of the reaction solutions. Specifically, the pH values of the reaction solutions were within the range of 7.0-8.0 after completion of the reaction with the cNDA in the reaction solutions. It is thus judged that the use of potassium phosphate (KH2PO4)-KOH buffer at a pH of 6.0-8.0 is most suitable.

In addition, the influence of potassium phosphate (KH2PO4)-KOH buffer on the composition of the reaction solutions was evaluated by varying the concentration of the potassium phosphate-KOH buffer solution from 0 to 100 mM. The results are shown in Table 10. The results show that no difference in the composition of the reaction solutions was observed despite changes in the concentration of the buffer solution.

TABLE 9

Changes in NDA content/FNA content in cNDA reaction solutions according to kind of buffer solutions

|  | Potassium phosphate ($KH_2PO_4$)—KOH buffer | Boric acid-NaOH | Sodium pyro-phosphate-HCl | Sodium borate-HCl |
|---|---|---|---|---|
| 0 | 91.09%/2.54% | 90.79%/2.69% | 90.81%/2.75% | 90.99%/2.65% |
| 15 min. | 92.68%/0.31% | 92.56%/0.39% | 92.29%/0.67% | 92.49%/0.44% |
| 30 min. | 93.23%/0% | 93.16%/0.02% | 93.04%/0.36% | 93.05%/0.16% |

TABLE 10

Changes in NDA content/FNA content in cNDA reaction solution with varying concentrations of potassium phosphate-KOH buffer

|  | 0 mM (D.W) | 20 mM | 50 mM | 100 mM |
|---|---|---|---|---|
| 0 | 91.12%/2.47% | 91.15%/2.62% | 91.09%/2.54% | 90.91%/2.65% |
| 15 min. | 92.65%/0.30% | 92.65%/0.37% | 92.68%/0.31% | 92.59%/0.34% |
| 30 min. | 93.20%/0% | 93.26%/0% | 93.23%/0% | 93.25%/0% |

TABLE 11

Amounts of bacteria required with varying cNDA concentrations at constant FNA content (4%) in cNDA

| | cNDA concentration (%) | | | |
|---|---|---|---|---|
|  | 5 | 6 | 7 | 10 |
| Amount of bacteria (g/L) | 40 | 50 | 50 | 87.5 |

TABLE 12

Amounts of bacteria required with varying cNDA concentrations at constant FNA content (1%) in cNDA

| | cNDA concentration (%) | | | | | |
|---|---|---|---|---|---|---|
|  | 5 | 6 | 7 | 8 | 9 | 10 |
| Amount of bacteria (g/L) | 10 | 10 | 20 | 37.5 | 50 | 75 |

Example 6

Initial pH of Reaction Solutions

Since the solubility of a cNDA increases with increasing pH, the pH of a reaction solution in the purification reaction of a cNDA is a very important reaction factor. In this experiment, the initial pH values of the reaction solutions having the composition indicated in Table 1 were varied within the range of 7.0 to 9.0. As a result, no reaction proceeded at a pH not higher than 7.5 and not lower than 8.3, indicating that the optimal pH range of the reaction solutions was between 7.5 and 8.3. Further, the optimal pH range for the cNDA purification reaction was found to be in the range of 7.8 to 8.1. In this pH range, little difference in the composition of the cNDA reaction solutions was observed after the reaction.

Example 7

Influence of FNA Content in cNDA, cNDA Concentration and Amount of Bacteria In this experiment, the purification reaction of a cNDA having different FNA contents ranging from 1% to 10% was conducted. The experimental results reveal that there was an intimate relationship among the FNA content in the cNDA, the concentration of the cNDA in the reaction solutions and the amount of the bacteria necessary to completely remove the FNA. That is, as the FNA content in the cNDA and the concentration of the cNDA in the reaction solutions increased, a larger amount of the bacteria (*Pseudomonas* sp. HN-72) was required to treat the FNA. Tables 11 and 12 show the amounts of the bacteria (*Pseudomonas* sp. HN-72) required at different FNA contents in the cNDA and different cNDA concentrations.

Example 8

Storage of Collected Bacteria (*Pseudomonas* Sp. HN-72)

Generally, the activity of microorganisms decreases with the passage of time after culturing. Accordingly, the maintenance of the activity of the bacteria as long as possible is advantageous for the purification method of the present invention. To maintain the activity of the cultured bacteria (*Pseudomonas* sp. HN-72) for a long period of time, the bacteria cultured under the conditions described in Example 1 were centrifuged, collected, and stored in a freezer at 4° C. or lyophilized. As a result, the activity of the bacteria was maintained even after storage in a freezer at 4° C. for 4 days. The bacteria could be stored for a longer period of time when lyophilized.

INDUSTRIAL APPLICABILITY

As apparent from the above description, the purification method using the *Pseudomonas* sp. HN-72 according to the present invention is economical and environmentally friendly, and enables the production of high-purity 2,6-naphthalene dicarboxylic acid. Therefore, the *Pseudomonas* sp. strain HN-72 of the present invention is very important for use in industrial applications.

The invention claimed is:

1. A method for purifying 2,6-naphthalene dicarboxylic acid using *Pseudomonas* sp. HN-72 Accession No. KCTC 10819BP, wherein the method comprises the steps of:
   1) inoculating the *Pseudomonas* sp. HN-72 onto a liquid medium, culturing the inoculum with shaking, collecting the cultured bacteria, and washing the collected bacteria with physiological saline to activate the bacteria;
   2) mixing a crude naphthalene dicarboxylic acid as a matrix with a buffer solution and adjusting the pH of the mixed solution to prepare a reaction solution for subsequent purification; and
   3) reacting the active bacteria prepared in step 1) with the reaction solution prepared in step 2) to convert 2-formyl-6-naphthoic acid contained in the crude naphthalene dicarboxylic acid to 2,6-naphthalene dicarboxylic acid, so that the purity of the 2,6-naphthalene dicarboxylic acid is increased.

2. The method according to claim 1, wherein the step of culturing the inoculum with shaking is performed at a temperature of 25 to 37° C.

3. The method according to claim 1, wherein the cultured bacteria collected after shaking is stored in a freezer at 4° C. or lyophilized.

4. The method according to claim 1, wherein the buffer solution is selected from the group consisting of potassium phosphate-KOH buffer, sodium pyrophosphate-HCl buffer, boric acid-NaOH buffer, and sodium borate-HCl buffer.

5. The method according to claim 1, wherein the buffer solution is potassium phosphate-KOH or boric acid-NaOH buffer.

6. The method according to claim 1, wherein the buffer solution has a concentration of 0.01 to 100 mM.

7. The method according to claim 1, wherein the pH of the mixed solution is adjusted to the range of 7.5 to 8.0.

8. The method according to claim 1, wherein the mixed solution further contains an organic solvent.

9. The method according to claim 8, wherein the organic solvent is selected from the group consisting of dimethylsulfoxide, N,N-dimethylformamide, N,N-dimethylacetamide, tetrahydrofuran, and mixtures thereof.

10. The method according to claim 8, wherein the organic solvent is added at a concentration of 0.01 to 10%.

11. The method according to claim 1, wherein, in step 3), the reaction is conducted in a temperature range of 30 to 50° C.

* * * * *

SEQUENCE LISTING

<160> NUMBER OF SEQ ID NOS: 1

<210> SEQ ID NO 1
<211> LENGTH: 700
<212> TYPE: DNA
<213> ORGANISM: Pseudomonas sp. HN-72

<400> SEQUENCE: 1

```
ttgcgagcgt gctacagcag tcagcggatg acgcgagctc gctccctgat tcagcggagg      60
acgggtgagt aatgcctagg attctggctg gtagtgggggg acaacgtctc gataggaacg     120
ctaataccgc atacgtccta cgtgagatag cattagacct tcggaccttg cgctatcaga     180
tgagccttgg tcggattagc tagatggtgc agtaatggct caggatggcg acgatccgta     240
actggtctga gaggatgatc actcacactg gaactgagac acggtccagg ctcctacgag     300
agcgggcagt ggtgaatatt ggacaatggg cgacagcctg atccaggcat gcagcgtgtg     360
tgaagaaggt cttcggattg taaagcactt taagttgtga ggaaggcgag taagttaata     420
ccttgctgtc atgacgttac cgaaagaata agcaccggct aactctgagc cagcagctgc     480
ggtaatacag atggtgcaag cgttaatcgg aattactggg cgtatagcgc gcgtaggtgg     540
tttgttaagt tggatgtgaa agccccgggc tcaacctggg aactgaatcc accactggca     600
agctagagta cggtagaggg tgctggaata tcctgtgtag cggtgaaatg cgtagatata     660
ggaaggaaca ccagtggcta cagcgaccac ctggactgat                            700
```